United States Patent
Sadozai et al.

(10) Patent No.: US 6,548,081 B2
(45) Date of Patent: Apr. 15, 2003

(54) BIOABSORBABLE COMPOSITES OF DERIVATIZED HYALURONIC ACID AND OTHER BIODEGRADABLE, BIOCOMPATIBLE POLYMERS

(75) Inventors: Khalid K. Sadozai, Shrewsbury, MA (US); Jing-wen Kuo, Wakefield, MA (US); Charles H. Sherwood, Sudbury, MA (US)

(73) Assignee: Anika Therapeutics, Inc., Woburn, MA (US)

( * ) Notice: Subject to any disclaimer, the term of this patent is extended or adjusted under 35 U.S.C. 154(b) by 0 days.

(21) Appl. No.: 09/863,029

(22) Filed: May 22, 2001

(65) Prior Publication Data

US 2002/0071855 A1 Jun. 13, 2002

Related U.S. Application Data

(60) Provisional application No. 60/222,116, filed on Jul. 28, 2000.

(51) Int. Cl.[7] .............................. A61F 2/02; A61K 47/30
(52) U.S. Cl. .................................... 424/426; 514/772.3
(58) Field of Search ................................. 424/423, 426; 514/772.3

(56) References Cited

U.S. PATENT DOCUMENTS

| | | | |
|---|---|---|---|
| 2,946,819 A | 7/1960 | Coles | 260/551 |
| 3,231,610 A | 1/1966 | Kühle | 260/551 |
| 3,502,722 A | 3/1970 | Neumann | 260/566 |
| 3,644,456 A | 2/1972 | Ulrich | 260/453 |
| 3,972,933 A | 8/1976 | Lawton | 260/566 |
| 4,014,935 A | 3/1977 | Ibbotson | 260/566 |
| 4,066,629 A | 1/1978 | Edelman | 260/77.5 |
| 4,085,140 A | 4/1978 | Ibbotson | 260/566 |
| 4,096,334 A | 6/1978 | Keil | 560/35 |
| 4,137,386 A | 1/1979 | Smith | 260/551 |
| 4,772,419 A | 9/1988 | Malson et al. | 252/315.1 |
| 4,897,349 A | 1/1990 | Swann et al. | 435/101 |
| 5,128,326 A | 7/1992 | Balazs et al. | 514/54 |
| 5,356,883 A | 10/1994 | Kuo et al. | 514/54 |
| 5,425,766 A | 6/1995 | Bowald | 623/13 |
| 5,502,081 A | 3/1996 | Kuo et al. | 514/777 |
| 5,567,806 A | 10/1996 | Abdul-Malak et al. | 530/356 |
| 5,766,631 A | 6/1998 | Arnold | 424/486 |
| 5,830,493 A | 11/1998 | Yokota et al. | 424/426 |
| 6,010,692 A | 1/2000 | Goldberg et al. | 424/78.06 |
| 6,013,679 A | 1/2000 | Kuo et al. | 514/777 |
| 6,056,970 A | 5/2000 | Greenawalt et al. | 424/426 |
| 6,096,727 A | 8/2000 | Kuo et al. | 514/54 |
| 6,129,757 A | 10/2000 | Weadock | 623/1.39 |

FOREIGN PATENT DOCUMENTS

| | | |
|---|---|---|
| EP | 0 612252 B1 | 8/1994 |
| EP | 0 705878 A2 | 10/1996 |
| JP | 7102002 | 4/1995 |
| WO | WO 86/04355 | 7/1986 |
| WO | WO 94/02517 | 3/1994 |
| WO | WO 97/07833 | 3/1997 |
| WO | WO 99/06079 | 11/1999 |

OTHER PUBLICATIONS

Wiseman, D.M., et al., "Fibrinolytic Drugs Prevent Pericardial Adhesions in the Rabbit," *J. Surg. Res.*, 53(4):362–368 (1992).

Arnold, P.B., et al., "Evaluation of Resorbable Barriers for Preventing Surgical Adhesions," *Fertil. Steril.*, 73(1):157–161 (2000).

Culliford, A.T., et al., "Angina Following Myocardial Revascularization," *J. Thor. Cardiovasc. Surg.*, 77(6):889–895 (1979).

English, T.A.H. and Milstein, B.B., "Repeat Open Intracardiac Operation," *J. Thor. Cardiovasc. Surg.*, 76(1):56–60 (1978).

Dobell, A.R.C and Jain, A.K., "Catastrophic Hemorrhage During Redo Sternotomy," *Ann. Thorac. Surg.*, 37(4):273–278 (1984).

Gallo, J.I., et al., "Clinical Experience with Glutaraldehyde-preserved Heterologous Pericardium for the Closure of the Pericardium After Open Heart Surgery," *Thorac. Cardiovasc. Surg.*, 30(5):306–309 (1982).

Minale, C., et al., "Closure of the Pericardium Using Expanded Polytetrafluoroethylene Gore–Tex®–Surgical Membrane: Clinical Experience," *Thorac. Cardiovasc. Surg.*, 35(5):312–315 (1987).

(List continued on next page.)

*Primary Examiner*—Carlos Azpuru
(74) *Attorney, Agent, or Firm*—Hamilton, Brook, Smith & Reynolds, P.C.

(57) ABSTRACT

The present invention relates to a composite and a method for reducing post-operative adhesion of tissues. The composite includes a biocompatible, biodegradable support, and a water-insoluble hyaluronic acid derivative at the support. The hyaluronic acid derivative includes an N-acylurea that results from cross-linking by the reaction of hyaluronic acid with a multifunctional carbodiimide. Optionally, a monocarbodiimide also may be employed. A pharmaceutically-active molecule may be added to the N-acylurea derivative of hyaluronic acid. Although the composite includes material that prevents adhesion between tissues, in order to reduce the need for suturing when the composite is being used during a surgical procedure, a material that enhances adhesion of the composite to tissues may be applied to a surface of the composite. A method of forming the composite for reducing post-operative adhesion of tissues, including the step of applying an N-acylurea derivative of hyaluronic acid resulting from cross-linking with a multifunctional carbodiimide, to a biocompatible, biodegradable support; a method of preparing a drug delivery vehicle that includes a pharmaceutically-active molecule with the N-acylurea derivative of hyaluronic acid resulting from cross-linking with a multifunctional carbodiimide; and a method of reducing post-operative adhesion of tissues are disclosed.

89 Claims, 1 Drawing Sheet

OTHER PUBLICATIONS

Harada, Y., et al., "Long–term Results of the Clinical use of an Expanded Polytetrafluoroethylene Surgical Membrane as a Pericardial Substitute," *J. Thorac. Cardiovasc. Surg.*, 96(5):811–815 (1988).

Okuyama, N., et al., "Prevention of Retrosternal Adhesion Formation in a Rabbit Model Using Bioresorbable Films of Polyethylene Glycol and Polylactic Acid," *J. Surg. Res.*, 78(2):118–122 (1998).

Malm, T. et al., "Prevention of Postoperative Pericardial Adhesions by Closure of the pericardium with Absorbable Polymer Patches. An Experimental Study," *J. Thor. Cardiovasc. Surg.*, 104(3):600–607 (1992).

Mitchell, J.D. et al., "Reduction in Experimental Pericardial Adhesions Using a Hyaluronic Acid Bioabsorbable Membrane ," *Eur. J. Cardiothorac. Surg.*, 8(3):149–152 (1994).

Kuo, Jing–wen, "Syntheses and Properties of Hyaluronic Acid Modified by Designed Carbodiimides," (Abstract), Dissertation Abstracts Intl. 50(12):5626–B (1990).

Diamond, M.P., "Reduction of de Novo Postsurgical Adhesions by Intraoperative Precoating with Sepracoat (HAL–C) Solution: A Prospective, Randomized, Blinded, Placebo–Controlled Multicenter Study," *Fertil. Steril.*, 69(6):1067–1074 (1998).

Hagberg, L., "Exogenous Hyaluronate as an Adjunct in the Prevention of Adhesions after Flexor Tendon Surgery: A Controlled Clinical Trial," *J. Hand Surg. [AM]*, 17A(1):132–136 (1992).

Becker, J.M., et al., "Prevention of Postoperative Abdominal Adhesions by a Sodium Hyaluronate–based Bioresorbable Membrane: A Prospective, Randomized, Double–Blind Multicenter Study," *J. Am. Coll.Surg.*, 183(4):297–306 (1996).

Johns, D.B. and diZerega, G.S., "Development and Clinical Evaluation of Intergel Adhesion Prevention Solution for the Reduction of Adhesions Following Peritoneal Cavity Surgery." *Peitoneal Surgery* (Springer–Verlag, New York) pp. 351–366 (1998).

Heydorn, M.D., et al., "A New Look at Pericardial Substitutes," *J. Thor. Cardiovasc.*, 94(2):291296 (1987).

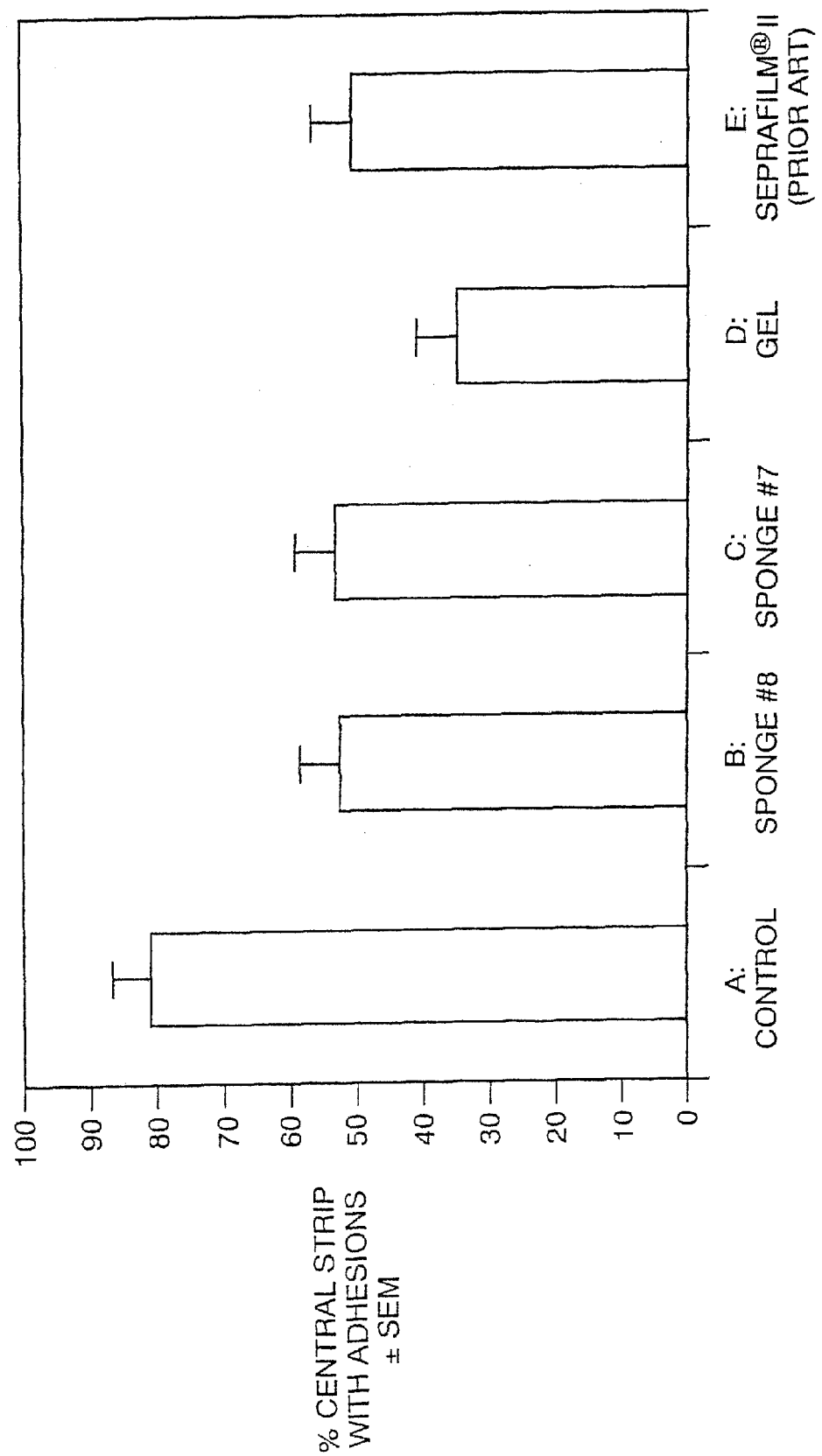

BIOABSORBABLE COMPOSITES OF DERIVATIZED HYALURONIC ACID AND OTHER BIODEGRADABLE, BIOCOMPATIBLE POLYMERS

RELATED APPLICATIONS

This application claims the benefit of U.S. Provisional Application No. 60/222,116, filed on Jul. 28, 2000, the entire teachings of which are incorporated herein by reference in their entirety.

BACKGROUND OF THE INVENTION

The formation of fibrovascular adhesions is a complication of surgery. The problems caused by these adhesions are varied and depend on the anatomical location of the surgical procedure. Peritoneal adhesions in abdominal surgery and peridural adhesions after laminectomy are two examples of this problem. In cardiac surgery, postoperative adhesions forming between the heart, pericardium and sternum, may place the mediasternal structures hazardously close to the path of dissection required in a subsequent procedure. Over 360,000 cardiac procedures are performed annually in the United States, of which 43,000 are re-operations (*J. Thor Cardiovasc. Surg.*, vol. 94, pp. 291–6 (1987)). Approximately 4% of patients undergoing re-operation experience complications, for example, hemorrhage, related to repeated sternal opening. If hemorrhage does occur, there is a mortality risk of approximately 37% (*Ann. Thorac. Surg.*, vol. 37, pp. 273–8.(1984)). Adhesion formation after cardiac surgery thus increases the costs and risks of a second cardiac procedure.

A number of methods have been evaluated to prevent adhesions after surgery. For example, in cardiac surgery, the placement of aldehyde-fixed xenografts, such as bovine pericardium, may calcify and fibrose, exacerbating the problem (*Thorac. Cardiovasc. Surg.*, vol. 30, pp. 306–9 (1982)). Animal studies have shown that the use of synthetic membranes is accompanied by a risk of closing the pericardium completely, and a risk of an accumulated pericardial effusion and tamponade (*J. Surg. Res.*, vol. 78, pp. 118–22 (1998)). Less rigid membranes are under development, but are less likely to reduce posterior/dorsal epicardial adhesions and would be difficult to use in thoracoscopic procedures. Overall, the medical need for an adhesion prevention material that can be placed over the heart via a thoracoscopic procedure has not been met.

In one type of articular surgery, in order to prevent accretions of cartilaginous tissue, rigid, non-bioabsorbable silicon plates are surgically introduced. The techniques presently available necessitate surgical removal of the plates, after a suitable period of time. There is a need for an adhesion prevention material which is rigid enough to be used in this type of articular surgery, but which does not have to be surgically removed.

Although it has exceptional biocompatibility, and has been used in a number of biomedical applications, native, uncross-linked hyaluronic acid ("HA") is generally not effective in reducing postoperative adhesions. Modified, water-insoluble derivatives of HA have been used as an aid to prevent adhesions or accretions of body tissues during the post-operation period. The method of forming the derivative, and its use in gels, films and sponges as surgical aids to prevent adhesions of body tissues and as drug delivery vehicles are described in U.S. Pat. No. 5,356,883 to Kuo et al., issued on Oct. 18, 1994. Generally, the method includes forming a water-insoluble gel by reacting HA, or a salt thereof, with a carbodiimide in the absence of a nucleophile or a polyanionic polysaccharide. The teachings of U.S. Pat. No. 5,356,883 are incorporated herein by reference in their entirety.

SUMMARY OF THE INVENTION

The present invention is directed to a composite and a method for reducing post-operative adhesion of tissues.

The composite includes a biocompatible, biodegradable support and hyaluronic acid derivative at the support. The hyaluronic acid derivative includes an N-acylurea that is formed by reaction of hyaluronic acid with a multifunctional carbodiimide. In another embodiment, at least 25 percent of derivatized functionalities of the hyaluronic acid derivative are O-acylisoureas or N-acylureas.

In still another embodiment, the invention is a drug delivery vehicle. The drug delivery vehicle includes a biocompatible-biodegradable support and a hyaluronic acid derivative component at the biocompatible-biodegradable support. The hyaluronic acid derivative component includes an N-acylurea that is formed by reaction of hyaluronic acid with a multifunctional carbodiimide. The drug delivery vehicle also includes a pharmaceutically active molecule at the hyaluronic acid derivative component.

In a further embodiment, the hyaluronic acid derivative component of the composite or the drug delivery vehicle is formed by reaction of hyaluronic acid with a multifunctional carbodiimide and a monocarbodiimide.

Another embodiment of the invention is a method of forming a composite for reducing post-operative adhesion of tissues. The method includes applying a hyaluronic acid derivative to a biocompatible-biodegradable support. The hyaluronic acid derivative includes an N-acylurea that results from reaction of hyaluronic acid with a multifunctional carbodiimide. In one embodiment, at least 25 percent of derivatized functionalities of the hyaluronic acid derivative are O-acylisoureas or N-acylureas.

In another embodiment, a method of preparing a drug delivery vehicle includes applying a hyaluronic acid derivative component to a biocompatible-biodegradable support. The hyaluronic acid derivative includes N-acylurea that results from reaction of hyaluronic acid with a multifunctional carbodiimide. The hyaluronic acid derivative component also includes a pharmaceutically-active molecule.

In another embodiment, a method of the invention includes forming a composite for reducing post-operative adhesion of tissue by applying a hyaluronic acid derivative component to a biocompatible-biodegradable support, wherein the hyaluronic acid derivative component includes an N-acylurea that is the reaction product of hyaluronic acid, a multifunctional carbodiimide, and a monocarbodiimide.

In still another embodiment, the method includes introducing to tissues at a surgical site a composite that includes a biocompatible-biodegradable support, and a derivatized hyaluronic acid component at the support. The derivatized hyaluronic acid component is the reaction product of hyaluronic acid and a multifunctional carbodiimide.

This invention has many advantages. For example, it provides a post-operative adhesion barrier that is at least substantially resorbable, and therefore generally does not need to be surgically removed at a later date. It also is relatively easy to use, is capable of being sutured, and tends to stay in place after it is applied. A further advantage is that it can supply modified HA in a sustained release manner over a prolonged period of time. The invention also provides a drug delivery system which can be easily injected or implanted at a particular site, where it provides sustained release of the drug.

BRIEF DESCRIPTION OF THE DRAWING

The FIGURE is a graph showing comparative test results in a rabbit model, for the effect of various embodiments of the invention, versus a comparative device and a control, on pericardial adhesion formation.

DETAILED DESCRIPTION OF THE INVENTION

The features and other details of the composite and method of the invention will now be more particularly described with reference to the accompanying FIGURE, and pointed out in the claims. It will be understood that the particular embodiments of the invention are shown by way of illustration and not as limitations of the invention. The principle features of this invention can be employed in various embodiments without departing from the scope of the invention. At the outset, the invention is described in its broadest overall aspects, with a more detailed description following.

Provided below are definitions of some of the terms used in the description. A "water-insoluble" gel, film or sponge of the invention, as that phrase and like terms are used herein, is one which is heterogeneous when suspended in a sufficient amount of water at room temperature.

A "biocompatible" substance, as that term is used herein, is one that has no medically unacceptable toxic or injurious effects on biological function.

A "biodegradable" substance, as that term is used herein, is one that is capable of being decomposed by natural biological processes.

A "nucleophile," as that term is used herein, is any molecule possessing an electron rich functional group (such as a primary amine).

A "polyanionic polysaccharide," as that term is used herein, is a polysaccharide other than HA containing more than one negatively charged group, e.g., a carboxyl group.

A "cross-linking agent," as that phrase is used herein, is a molecule containing two or more functional groups that can react with HA or a derivative thereof.

A "film," as that term is used herein, means a substance formed by compressing a gel or by allowing or causing a gel to dehydrate. A gel of the invention may be formed into such a film.

A "sponge," as that term is used herein, means a substance formed by freeze-drying a gel. A gel of the invention may be formed into such a sponge.

"Room temperature," as that phrase is used herein, includes temperatures in the range of from about 20° C. to about 25° C.

As used herein, the term "HA" means hyaluronic acid and any of its hyaluronate salts, including, but not limited to, sodium hyaluronate (the sodium salt), potassium hyaluronate, magnesium hyaluronate, and calcium hyaluronate.

"Derivatized hyaluronic acid," as the term is used herein, means hyaluronic acid that has been derivatized with a carbodiimide, such as a monocarbodiimide or a multifunctional carbodiimide, or that has been derivatized with a mixture of a multifunctional carbodiimide and a monocarbodiimide. Preferably the derivatization is carried out in the absence of a polyanionic polysaccharide other than the hyaluronic acid. In a specific embodiment, the derivatized hyaluronic acid is water-insoluble.

An embodiment of a composite of the invention includes at least two components: a biocompatible, biodegradable support and a derivative of HA that includes an N-acylurea resulting from cross-linking with a multifunctional carbodiimide, such as a biscarbodiimide.

Examples of the physical form of a suitable support include: a biocompatible, biodegradable matrix, sponge, film, mesh, and a composite of particles which may be in the form of beads. The beads may be bound together by a bioabsorbable material. The biodegradable support may be formed from a material which is porous, and the pore sizes may be large enough so that when a layer of the hyaluronic acid (HA) derivative is spread on the support, the molecules of the HA derivative can partially or fully penetrate into the pores of the support to make an anchor. Examples of compositions to be used as a suitable support include: cross-linked alginates, gelatin, collagen, cross-linked collagen, collagen derivatives, such as, succinylated collagen or methylated collagen, cross-linked hyaluronic acid, chitosan, chitosan derivatives, such as, methylpyrrolidone-chitosan, cellulose and cellulose derivatives such as cellulose acetate or carboxymethyl cellulose, dextran derivatives such carboxymethyl dextran, starch and derivatives of starch such as hydroxyethyl starch, other glycosaminoglycans and their derivatives, other polyanionic polysaccharides or their derivatives, polylactic acid (PLA), polyglycolic acid (PGA), a copolymer of a polylactic acid and a polyglycolic acid (PLGA), lactides, glycolides, and other polyesters, polyoxanones and polyoxalates, copolymer of poly(bis(p-carboxyphenoxy)propane)anhydride (PCPP) and sebacic acid, poly(1-glutamic acid), poly(d-glutamic acid), polyacrylic acid, poly(d1-glutamic acid), poly(1-aspartic acid), poly(d-aspartic acid), poly(d1-aspartic acid), polyethylene glycol, copolymers of the above listed polyamino acids with polyethylene glycol, polypeptides, such as, collagen-like, silk-like, and silk-elastin-like proteins, polycaprolactone, poly(alkylene succinates), poly(hydroxy butyrate) (PHB), poly(butylene diglycolate), nylon-2/nylon-6-copolyamides, polydihydropyrans, polyphosphazenes, poly(ortho ester), poly(cyano acrylates), polyvinylpyrrolidone, polyvinylalcohol, poly casein, keratin, myosin, and fibrin. A sample of highly cross-linked HA may form a support for a sample of modified HA which is not highly cross-linked.

In general, the modified HA derivative is prepared by reacting hyaluronic acid, or a salt thereof, with a multifunctional carbodiimide, preferably a biscarbodiimide, in the absence of a nucleophile or a polyanionic polysaccharide other than HA, to form an N-acylurea resulting from cross-linking with the multifunctional carbodiimide. Additionally, a monocarbodiimide may be employed in combination with a multifunctional carbodiimide, the monocarbodiimide having the formula:

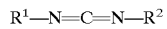

wherein $R^1$ and $R^2$ may include hydrocarbyl, substituted-hydrocarbyl, alkoxy, aryloxy, alkaryloxy. Examples of suitable monocarbodiimides include: 1-ethyl-3-(3-dimethylaminopropyl)-carbodiimide hydrochloride (EDC); 1-cyclohexyl-3-(2-morpholinoethyl)carbodiimide metho-p-toluenesulfonate (CMC); 1-(3-(dimethylamino)propyl)-3-ethylcarbodiimide methiodide (EAC); 1,3-dicyclohexylcarbodiimide (DCC); and 1-benzyl-3-(3-dimethylaminopropyl) carbodiimide hydrochloride (BDC).

Use of a polycarbodiimide to prepare the modified HA derivative causes cross-linking of the hyaluronic acid. For example, use of a biscarbodiimide reactant to prepare the water insoluble gel of the invention results in a cross-linking between COOH groups present on the repeating disaccharide unit of hyaluronic acid, since the biscarbodiimide is difunctional. The COOH group may be present in the same polymer chain, resulting in an intramolecular cross-linked product, or present on two different polymer chains, resulting in an intermolecular cross-linked product.

Examples of suitable biscarbodiimides may be represented by those difunctional compounds having the formula: $R^1$—N=C=N—$R^2$—N=C=N—$R^3$, wherein $R^1$, $R^2$ and $R^3$ may include hydrocarbyl, substituted-hydrocarbyl, alkoxy, aryloxy, alkaryloxy and the like.

The term "hydrocarbyl" as used herein means the monovalent moiety obtained upon removal of a hydrogen atom from a parent hydrocarbon. Representatives of hydrocarbyls are alkyls of 1 to 25 carbon atoms, inclusive, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonodecyl, eicosyl, heneicosyl, docosyl, tricosyl, tetracosyl, pentacosyl and the isomeric forms thereof; aryl of 6 to 25 carbon atoms, inclusive, such as phenyl, tolyl, xylyl, naphthyl, biphenylyl, triphenylyl, and the like; aryalkyl of 7 to 25 carbon atoms, inclusive, such as benzyl, phenylethyl, phenylpropyl, phenylbutyl, phenylhexyl, naphthylalkyl and the like; cycloalkyl of 3 to 8 carbon atoms, inclusive, such as cyclopropyl, cyclobutyl, cyclopentyl, cyclohexyl, cycloheptyl, cyclooctyl and the like; alkenyl of 2 of 25 carbon atoms, inclusive, such as vinyl, allyl, butenyl, pentenyl, hexenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, and isomeric forms thereof. Preferably, hydrocarbyl has 6 to 14 carbon atoms, inclusive.

The term "substituted hydrocarbyl" as used herein means the hydrocarbyl moiety as previously defined wherein one or more hydrogen atoms have been replaced with a chemical group which does not adversely affect the desired preparation of the product derivative. Representative of such groups are amino-, phosphino-, quaternary nitrogen (ammonium), quarternary phosphorus (phosphonium), hydroxyl, amide, alkoxy, mercapto, nitro, alkyl, halo, sulfone, sulfoxide, phosphate, phosphite, carboxylate, carbamate groups and the like. Preferred groups are amino, amide, ester, and ammonium groups.

Preferred N-acylureas and O-acylisoureas of the invention are those in which $R^1$ and/or $R^2$ are hydrocarbyl substituted with an amino group. The term "alkoxy" as used herein means a monovalent group of the formula:

—O-alkyl wherein the alkyl preferably has 4 to 12 carbon atoms, inclusive. The term "aryloxy" as used herein means the monovalent group of the formula:

—O-aryl wherein the aryl preferably has 6 to 10 carbon atoms, inclusive and may be substituted as described above. The term "alkylaryloxy" as used herein means the monovalent group of formula:

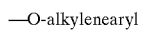
—O-alkylenearyl such as oxybenzyl and the like.

Preferred biscarbodiimides include p-phenylene bis (ethylcarbodiimide) and 1,6-hexamethylene bis (ethylcarbodiimide). Other examples of suitable biscarbodiimides include 1,8-octamethylene bis(ethylcarbodiimide); 1,10 decamethylene bis(ethylcarbodiimide); 1,12 dodecamethylene bis(ethylcarbodiimide); PEG-bis(propyl (ethylcarbodiimide)); 2,2'-dithioethyl bis (ethylcarbodiimide); 1,1'-dithio-p-phenylene bis (ethylcarbodiimide); and 1,1'-dithio-m-phenylene bis (ethylcarbodiimide).

The reaction of HA with a biscarbodiimide rather than a monocarbodiimide does not change the mechanism of reaction, but causes the product to be cross-linked.

Those skilled in the art will know, or will be able to ascertain with no more than routine experimentation, methods of preparing suitable biscarbodiimides. See, for example, the methods described in U.S. Pat. Nos. 6,013,679; 2,946,819; 3,231,610; 3,502,722; 3,644,456; 3,972,933; 4,014,935; 4,066,629; 4,085,140; 4,096,334; and 4,137,386, all of which are incorporated herein by reference in their entirety.

In one embodiment, the reaction is carried out under conditions such that the resulting modified hyaluronic acid product is at least about 1% cross-linked. The conditions necessary to achieve at least about 1% cross-linking, are first described in general, and further and specifically described in the Examples. In another embodiment, at least about 2% of the carboxyl functionalities of the modified hyaluronic acid are derivatized. Generally, at least about 25% of the derivatized functionalities are O-acylisoureas or N-acylureas. Examples of sets of conditions that achieve at least about 2% derivatization are specifically described in the Exemplification section.

The steps required to make a biocompatible HA derivative of this invention include providing a sample of HA or a salt thereof, such as sodium hyaluronate. HA from any of a variety of sources, including HA extracted from animal tissues or harvested as a product of bacterial fermentation, can be used as a starting material. Alternatively, the HA used to make the composites of this invention can be produced in commercial quantities by bioprocess technology, as described, for example, in Nimrod et al., PCT Publication No. WO 86/04355. The sample of HA or its salt is dissolved in water to make an aqueous solution. Preferably, the concentration of HA in this first aqueous solution is in the range of between about 0.1% and 5% weight/weight ("w/w"), that is, 1 mg/ml solution to 50 mg/ml solution. More preferably, the reactions are carried out with a range of about between about 0.4% and 0.6%, or 4 to 6 mg of hyaluronic acid per milliliter. The precise concentration used will vary depending on the molecular weight of the HA. At significantly lower concentrations, the reactions are slower and less effective. At significantly higher HA concentrations, the end product may be difficult to handle due to the increase in viscosity. One skilled in the art will be able to determine, with no more than routine experimentation, an acceptable concentration of HA to be used for a particular embodiment. Examples of acceptable concentrations of HA are described in U.S. Pat. No. 5,356,883, to Kuo et al., the teachings of which are incorporated herein by reference in their entirety.

The pH of the HA solution is then adjusted by the addition of a suitable acid, so that the aqueous HA solution is acidic, preferably having a pH of about between 4.0 and 6.0, more preferably between about pH 4.75 and about pH 5.5.

Once the pH of the aqueous HA solution has been adjusted, the carbodiimide can be added. Generally an excess of the stoichometric proportion of carbodiimide is advantageous to promote the desired reaction. Preferably the molar equivalent ratio of the carbodiimide to HA is equal to or greater than about 5%.

Preferably, the carbodiimide is dissolved in an appropriate water-mixable solvent and added drop-wise. As the carbodiimide and the HA are mixed, the pH of the solution generally will increase. Films and gels with various desired physical properties can be obtained by simply allowing the pH to rise as the reaction proceeds. However, the reaction is monitored by a pH meter, and HCl may be added to maintain the pH of the reaction mixture between about 4.75 and about 5.50. The reaction is allowed to proceed at room temperature for about two hours.

The details of the reaction are described in U.S. Pat. Nos. 6,013,679, and 5,356,883, the contents of which are incorporated herein by reference in their entireties.

The reaction conditions for HA cross-linking with a biscarbodiimide are similar to those used for HA-monocarbodiimide coupling reactions. Advantageously, the cross-linking reactions are carried out with (1) an increase of the HA concentration in the reaction mixture, and (2) a decrease of the biscarbodiimide concentration in the addition solution. This creates a condition favorable to intermolecular cross-linking versus intramolecular cross-linking.

The reactions described above may be directed to favor the formation of the N-acylurea derivatives by increasing the pH with aqueous base.

The progress of the reaction described above may be followed by monitoring the pH. When the pH is stabilized, the reaction is substantially complete. At the conclusion of the reaction, the desired hyaluronic acid derivative may be separated from the reaction mixture by conventional methods of precipitation, washing and re-precipitation. The completeness of the reaction, the nature of the products and the extent of chemical modification can be determined by proton NMR.

If a colored product is desired, a solution of a biocompatible dye or stain, e.g., Coomassie™ Brilliant Blue R-250, can be admixed to the reaction mixture. The resulting product will have a blue color which makes the gel, film or sponge easy to see when it is handled during surgery and when it is in place.

When the reaction is complete, sodium chloride is added to the reaction mixture to adjust the sodium chloride concentration to 1M. Ethanol equal to three volumes of the reaction mixture is added to form a white, stringy precipitate of chemically-modified, HA derivative. The precipitate is separated from the solution, washed, and dried by vacuum.

To make a water-insoluble gel of the HA derivative, the precipitate is re-suspended in water and stirred in a cold room. The gel of the HA derivative is a hydrogel. The term "hydrogel" is defined herein to mean a macromolecular network swollen in water or biological fluids. The degree of gelation is dependent on the degree of cross-linking achieved.

To make a sponge, the precipitate is then re-suspended in water, poured into a mold having a desired shape, and, preferably, dried, such as by air-drying, freeze-drying or heat-drying. A film may be prepared by further drying the gel. Alternatively, a film can be formed by compressing a gel under conditions that permit water to escape, as, for example, by compressing the gel between two surfaces, at least one of which is porous. See, for example, Malson et al., U.S. Pat. No. 4,772,419, the teachings of which are incorporated herein by reference in their entirety.

There are several ways in which the gel, film or sponge can be immobilized on the support to make the composite device of this invention. For example, a layer of derivatized, cross-linked hyaluronic acid may be applied, either by soaking or dipping or spraying or spreading or by any other method of application, to at least one surface of a support to form a composite. A suitable support may be a matrix, sponge, film, or particles such as beads, which may be porous. If the surface of the support is porous, the HA derivative will soak into the pores on the support surface. For example, porous beads may be soaked in the hyaluronic acid derivative for a sufficient period of time to allow the hyaluronic acid derivative to be absorbed and adsorbed by the pores of the beads. The composite is then dried under conditions that permit the escape of water from the composite.

The dried beads may be suspended in a solution of a solvent and a second biopolymer, for example, polylactic—polyglycolic acid—copolymer (PLGA). The suspension may then be poured into a mold, and the solvent allowed to evaporate. The composite thus formed will have the beads of derivatized HA and first biopolymer entrapped in a fine film of a second biopolymer.

Dried beads may be compressed to form a sheet. The product is thus a composite sponge or film in which derivatized HA has formed a uniform layer in contact with at least a portion of the surface of the support. If the surface of the support is porous, a portion of the layer of derivatized HA is embedded and anchored into the surface of the support.

In another embodiment, a composite sponge or film having hyaluronic acid derivative on both sides of the support is prepared by pouring the water-insoluble gel of derivatized HA prepared according to the procedure described above, into a first mold having the desired shape and depth, and spreading the gel in the first mold to form a first gel layer of even thickness. A suitable support may be a matrix, sponge, film, or particles such as beads made from another biocompatible material, for example collagen or gelatin. The support is spread on top of the evenly-spread first gel layer of derivatized HA. A second mold of the same size, shape and depth, is placed on the top of the support. Gel is poured into the second mold, and spread to form a second gel layer of even thickness in the second mold. In this manner, the polymer used as supporting matrix is sandwiched between the two layers of derivatized HA gel which are molded to the support. The composite is freeze-dried. The freeze-dried composite is compressed and cut into specimens of the desired shape and size.

To make a composite having derivatized HA gel on one side of the composite and a different material on another side, the second mold can be filled with a different kind of gel. The composite that is formed will have derivatized HA on one side and the different material on another side. This embodiment of the invention provides a composite that could have a coating on one side that enhances adherence of the composite to wet tissue, and a coating on another side that prevents adhesion between tissues. Materials that are suitable for enhancing adherence of the composite to tissue include fibrin, collagen, cross-linked collagen, and collagen derivatives, and any other polymers containing the peptide sequence, arginine (R), glycine (G), and aspartic acid (D). In surgical sites where suturing is not possible, and keeping the composite in place is difficult, this composite may stay in place just by adhering to the tissue. Suturing may not be required.

These composites provide a sustained source of derivatized HA at the surgical site as the composite biodegrades and is absorbed by the tissues. The rate of biodegradation, and thus the rate of release of derivatized HA can be controlled, in part, by the degree of cross-linking of HA, and the quantity of the cross-linked HA loaded on the support. The residence time of unmodified HA in the human body is generally less than a week. However, when HA is derivatized, the residence time is appreciably increased. In general, an increase in the degree of cross-linking results in an increase in the time of residence. By controlling the degree of cross-linking, a cross-linked HA of desired residence time can be synthesized. Furthermore, coating the derivatized HA on a porous, biodegradable support enables the derivatized HA to penetrate into the pores of the support. When the derivatized HA present on the surface of the support is degraded, there is still some derivatized HA present in the pores of the support. Following the biodegradation of the derivatized HA present on the surface of the composite, the biodegradable matrix also degrades. During the degradation of the matrix, the derivatized HA trapped in the pores of the matrix is released and thus provides a sustained supply of derivatized HA. After the resorption and degradation of the composite, the healed tissues come into contact with each other and resumé their normal function. The derivatized HA selected for a particular use may have a biodegradation rate which is faster than the biodegradation rate of the support. The support, in fact, can be itself made of a sample of cross-linked HA having a slower rate of biodegradation than that of the derivatized HA loaded on the support.

The rate at which the gel, film or sponge degrades and diffuses also depends on the insolubility, the density, and the degree of cross-linking of the modified HA in the composite. Just as gels, films and sponges which have a high degree of cross-linking are slow to degrade, modified HA which is more insoluble, or which has a higher degree of cross-linking, will degrade at a slower rate. Preferably, the density of modified HA in the film or sponge will be in the range of from about 0.1 mg/cm$^2$ to about 10 mg/cm$^2$. Those skilled in the art will know, or will be able to ascertain with no more than routine experimentation, the appropriate combination of insolubility, density and cross-linking that will yield a gel, film or sponge having the desired rate of degradation for a given situation.

The composite structure can be used as a surgical aid to separate healing tissues or to prevent post-operative adhesion. Introduced to the tissues, either during surgery or post-operatively, the gel, film, or sponge made of derivatized HA according to the procedure described above, gets re-hydrated and forms a swollen gel. This swollen composite, placed between or among the tissues, keeps the healing tissues separated from each other and maintains the said separation during the healing process. The support matrix helps the composite stay in place. Preferably, the composite structure should remain in place for a long enough period so that when it has entirely degraded and dispersed and the tissues do come into contact, the tissues will no longer have a tendency to adhere. The length of the post-operative period during which a contact-inhibiting effect between tissues should be maintained varies according to the type of surgery involved.

Examples of surgical procedures in which the biocompatible gels, films and sponges of this invention may be used include, but are not limited to, cardiosurgery, operations performed in abdominal regions where it is important to prevent adhesions of the intestine or the mesentery; operations performed in the urogenital regions where it is important to ward off adverse effects on the ureter and bladder, and on the functioning of the oviduct and uterus; and nerve surgery operations where it is important to minimize the development of granulation tissue. In surgery involving tendons, there is generally a tendency towards adhesion between the tendon and the surrounding sheath or other surrounding tissue during the immobilization period following the operation.

In ophthalmological surgery, a biodegradable implant could be applied in the angle of the anterior chamber of the eye for the purpose of preventing the development of synechiae between the cornea and the iris; this applies especially in cases of reconstructions after severe damaging events. Moreover, degradable or permanent implants are often desirable for preventing adhesion after glaucoma surgery and strabismus surgery.

In yet another embodiment, this invention is directed to drug delivery systems. Free functional groups in the acylurea side-arm (e.g., amines, amides, and esters) can be further reacted to bond with reactive therapeutic drug molecules, under conventional and known reaction conditions, to obtain vehicles for delivery of therapeutic drugs. For example, hydrophobic and/or cationic "sidearms" may be attached to the HA polymer, to prepare useful polymer carriers for therapeutic drugs. In carrying out the preparation of the derivatized HA of the invention, a sufficient proportion of the carbodiimide is reacted with the HA, or salt thereof, to obtain a polymer chain having recurring polymer chain units, interrupted by at least one disaccharide unit per HA molecule having a pendant acylurea side-arm. See, for example, U.S. Pat. No. 5,356,883, to Kuo et al., the teachings of which are incorporated herein by reference in their entirety. The biscarbodiimide cross-linked hyaluronic acid possesses new drug-binding regions which do not interfere with biocompatibility.

A controlled-release drug delivery vehicle can be formed from a pharmaceutically-active substance, such as a therapeutic drug, which covalently bonds to, or noncovalently interacts with, the modified HA polymer of the invention. The non-covalent interactions include ionic, hydrophobic, and hydrophilic interactions in which the drug is dispersed within the gel, film or sponge. As used herein, the term "dispersed" shall refer to ionic, hydrophobic, and hydrophilic interactions between the drug and the modified HA. For example, by selection of appropriate carbodiimides, such as 1-ethyl-3-(3-dimethylaminopropyl)-carbodiimide hydrochloride (EDC), a cationic moiety can be immobilized on HA polymer chains. This cationic site may serve as a noncovalent, ionic binding site for anionic substances such as non-steroidal anti-inflammatory drugs (e.g. naprosyn). In both cases, the modified HA functions as a vehicle which provides the controlled release of a drug from the system. In both cases, the drug delivery system is then injected or implanted at the locus where delivery is desired.

Any substance which has biological or pharmaceutical activity and which is normally considered to be a drug can be used as the drug component in the delivery systems of the invention. The choice of the substance will depend upon the specific use of the drug delivery system. Suitable pharmaceutically-active substances include growth factors, enzymes, therapeutic drugs, biopolymers, and biologically compatible synthetic polymers.

A "therapeutic drug," as that term is used herein, includes, for example: compounds and compositions recognized in the official United States Pharmacopoeia, the official Homeopathic Pharmacopoeia of the United States, or the official National Formulary, or any supplement of any of them; compounds and compositions intended for use in the diagnosis, cure, mitigation, treatment, or prevention of disease in man or other animals; and compounds and compositions (other than food) intended to affect the structure or any function of the body of man or other animals.

Examples of classes of therapeutic drugs include steroidal and non-steroidal anti-inflammatory drugs, hormones and any synthetic analogues and pharmaceutically-active fragments thereof.

Therapeutic drugs which are suitable for use in the delivery system of the invention may be fat soluble, water-soluble, anionic or cationic, as long as they can interact with a group on the carbodiimide residue to form either covalent or ionic bonds or hydrophobic or hydrophilic interactions, including those described below.

A hydrophobic interaction between the drug and the modified HA can occur when, by appropriate selection of the carbodiimide, the hydrophilic HA is controllably converted in character to include a hydrophobic entity which is receptive to further interaction with a therapeutic drug having a hydrophobic moiety. Suitable drugs include fatty acid derivatives, steroids (e.g., dexamethasone) and their analogs, and other drugs with hydrophobicity.

The delivery system of the invention is particularly well-suited for administering growth factors (e.g., interleukins, prostaglandins, thromboxanes, leukotrienes and cytokines), steroidal and non-steroidal contraceptive agents, antibiotics (e.g., penicillin, streptomycin and linocomycin), analgesics, sedatives, barbiturates, aminoalkylbenzenes, catecholamines, narcotics, narcotic antagonists, antineoplastic agents and anticoagulants (e.g., heparin and heparin sulfate).

The drug concentration can be varied over very broad limits and preferably should be chosen depending on the solubility of the drug, its pharmaceutical activity, and the effect desired.

Those skilled in the art will appreciate that the functional carboxylic acid group of unmodified HA is sheltered by the molecule conformation, making it slow to react, it at all. The modified HA of this invention, however, is an HA acylurea which possesses at least one "side-arm" or "spacer" projecting outwardly from the polymer chain. This outwardly projecting side-arm includes one or more reactive sites, depending on the carbodiimide employed. The reactive site(s) include, at the least, a primary or secondary amino, amide, imino or ammonium group. The availability of a free amino group provides a reaction site free of steric hindrance associated with the polymer chain. This reaction site may then be used to couple the water-insoluble compositions of the invention to a therapeutic drug. For example, a primary amine-functionalized HA can be used as a tether for drug coupling. A carboxylate-containing anti-inflammatory drug, such as Ibuprofen (2-methyl-4-(2-methyl-propyl) benzeneacetic acid), can be converted to the corresponding N-hydroxysuccinimide (NHS) active esters, which can react with the primary amine under physiological conditions.

Peptides can also be linked to the amine tether of an amine-functionalized HA. A thiol-cleavable cross-linker such as dithiobis(succinimidyl)-propionate (DSP) is first used to cross-link the amine tethers of modified HA. Then, the sulfhydryl groups produced through the reduction of the disulfide bonds can react with the e-amino group of lysine of the peptides through the heterobifunctional cross-linker N-succinimidyl-3-(2-pyridyldithio) propionate (SPDP).

Alternatively, therapeutic drugs containing reactive functional groups (e.g., hydroxyl, carboxyl, amino) can be covalently bonded to the carbodiimide prior to reaction with HA to form hydrolyzable bonds. Then, the carbodiimides which contain drugs can be attached to HA via the acylurea linkage. For example, a carboxyl-containing therapeutic drug can react with a carbodiimide precursor, e.g., a thiourea, bearing a pendant amine or hydroxyl group to tether the drug through an enzymatically labile amide or ester linkage. The resulting thiourea may then be converted to the corresponding carbodiimide. Upon reaction of the carbodiimide with the hyaluronic acid, a drug delivery system is obtained without further reactions.

There are generally two chemical interactions in the drug delivery systems of the invention. The first is a very stable acylurea linkage between the modified HA molecule and the carbodiimide moiety. The second is a less stable linkage or interaction between the carbodiimide moiety and the therapeutic drug moiety. The less stable linkage is readily broken, releasing the therapeutic drug at the site of administration. The more stable chemical bond between the HA molecule and the carbodiimide moiety will ensure the release of the therapeutic drug without the release of the carbodiimide residue, which might affect the therapeutic action of the drug.

Delivery is also related to the degradation of the gel, film or sponge as a result numerous metabolic processes taking place in vivo. The degradation process is usually slower than diffusion, which provides the delivery of a drug via delivery systems in which the drug non-covalently interacts with the derivatized HA of the gel, film or sponge vehicle. By choosing the concentration of derivatized HA, one can control the rate of degradation or diffusion and, thus, the rate of drug delivery.

The modification of the HA by reaction with a carbodiimide does not adversely degrade the polymer. At a low degree of chemical modification, the properties of viscoelasticity may be retained to produce a soluble product. One skilled in the art will know, or will be able to ascertain with no more than routine experimentation, the degree of chemical modification necessary to yield an insoluble gel.

The drug delivery products of the invention can be administered to a mammal, including humans, in pharmaceutically-acceptable dosage forms, with or without the use of pharmaceutically-acceptable carriers. Dosage forms include, but are not limited to, intravenous, intra-articular, sub-cutaneous, oral and topical administration forms.

In mammals, the majority of free HA in the body is taken up in the lymphatic system, this is especially true for the higher molecular weight HA. The HA circulating in the human body has a medium molecular weight in the range of $1.4 \times 10^5$ to $2.7 \times 10^5$ and is taken up by liver endothelial cells. HA with a molecular weight less than $2.5 \times 10^4$ is within the filtration limit of human kidneys and is excreted in urine. Accordingly, one advantageous use of the composite for the treatment of certain neoplastic disease is an intravenous administration of an acylurea-cytotoxin combination, releasing the therapeutic drug at the site of neoplastic incursions. Also, by the selection of HA having an appropriate molecular weight, the kidneys can be targeted for drug administration.

The invention is described in more detail in the following examples. These examples are given by way of illustration and are not intended to limit the invention in any way.

EXEMPLIFICATION

Example 1

This example illustrates an embodiment of the invention in which a biscarbodiimide, p-phenylene-bis (ethylcarbodiimide), and HA are reacted at a molar equivalent ratio of 16.7%, to yield a water-insoluble gel.

A solution of HA (6 mg/ml; 1130-ml; 16.9 mequiv) was reacted with a solution of p-phenylene-bis (ethylcarbodiimide) (1 mg/ml in acetone; 302-ml; 1.4 mmol; 2.8 mequiv) according to a procedure described in U.S. Pat. Nos. 5,356,883, 5,502,081 and 6,013,679, the teachings of which are incorporated herein by reference in their entirety. The precipitate of the cross-linked HA was separated from the solution, washed, and resuspended in saline. The suspension was stirred for 2 days in a cold room to form a water-insoluble gel of ~4 mg/ml concentration. Chloroform equal to ½ of the volume of the aqueous solution was added to the solution and contents were vigorously stirred for seven days in the cold room. The reaction mixture was then centrifuged at 4° C. and 43 k rpm for one hour to remove chloroform. The aqueous/gel layer was aseptically collected and the concentration of sodium chloride in the collected aqueous/gel was adjusted to 1M. The mixture was stirred for 15 minutes under aseptic conditions. Ethanol equal to 3 volumes of the solution was added to precipitate the cross-linked HA and the precipitate was collected, squeezed to remove ethanol, and shredded into small pieces under aseptic conditions. The precipitate was re-dissolved in injection grade water to reconstitute a gel of desired concentration.

Example 2

Example 2 describes the preparation of Sponge 1, an embodiment of the invention which is a composite including cross-linked HA only. To make Sponge 1, a gel of cross-linked HA prepared according to the procedure described in Example 1, was poured into an 8 cm×8 cm mold under aseptic conditions. The mold containing the cross-linked HA gel was frozen at −45° C. and then freeze-dried for 24 hours under vacuum of less then 10 millimeters. The freeze-dried sponge was compressed under aseptic conditions and cut into 4 cm×4 cm pieces. These sponges were put in sterile pouches and sealed to keep them sterile. The amount of cross-linked HA present in Sponge 1 was 6.1±0.8 mg/cm$^2$.

Example 3

Example 3 describes the preparation of Sponge 2, an embodiment of the invention which is a composite including cross-linked HA on both sides of a porous, pliable, biocompatible, biodegradable support made of purified pork gelatin. The support used to make Sponge 2 is commercially available from the Upjohn Company, and is sold under the name, Gelfoam®. (Gelfoam® is a registered trademark of the Upjohn Company. It is available as a sterile sponge of various dimensions for application to bleeding surfaces as a hemostatic. Gelfoam® is a porous, non-elastic, pliable product prepared from purified pork skin gelatin USP granules and water for injection.) A 12.5 cm×8 cm piece of sterile Gelfoam® was soaked for 3 hours in cross-linked HA gel prepared according to the procedure described in Example 1. The soaked sponge, having a layer of cross-linked HA on both sides, was spread in a sterile petri dish and frozen at −45° C. and then freeze-dried for 24 hours under a vacuum of less then 10 millimeters. The freeze-dried sponge was compressed under aseptic conditions and cut into 4 cm×4 cm pieces. These sponges were put in sterile pouches and sealed to keep them sterile. The amount of cross-linked HA present on both sides of Sponge 2 was 4.7±0.8 mg/cm$^2$.

Example 4

Example 4 describes the preparation of Sponge 3, an embodiment of the invention which is a composite including cross-linked HA on both sides of a porous, pliable, biocompatible, biodegradable support made of purified pork gelatin. The pork gelatin used is commercially available under the registered trademark name, Gelfoam®, from the Upjohn Company. A 12.5 cm×8 cm piece of sterile Gelfoam® was soaked for 3 hours in cross-linked HA gel of 3-mg/ml concentration. The soaked sponge, having a layer of cross-linked HA on the both sides, was spread in a sterile petri dish and frozen at −45° C. and then freeze-dried for 24 hours under a vacuum of less then 10 millimeters. The freeze-dried sponge was compressed under aseptic conditions and cut into 4 cm×4 cm pieces. These sponges were put in sterile pouches and sealed to keep them sterile. The amount of cross-linked HA present on the Sponge 3 was 1.3±0.5 mg/cm$^2$.

Example 5

Example 5 describes the preparation of Sponge 2A, an embodiment of the invention which is a composite including cross-linked HA on both sides of a porous, pliable, biocompatible, biodegradable support made of collagen from bovine tendon. The collagen used to make the support for Sponge 2A is commercially available from Integra-LifeSciences, and was one-half the density of the normal collagen sponges sold under the name, Helistat®. (Helistat® is a registered tradename of Integra-LifeSciences.)

The tendon collagen matrix was cut into 4.4 cm×4.4 cm square pieces. These pieces were heat sterilized in a vacuum oven at 140° C. for 4 hours. After cooling under aseptic conditions, cross-linked HA gel (6.8 mg/ml, 3±0.1 ml), prepared according to the procedure described in Example 1, was poured in to a 4.4 cm×4.4 cm mold under aseptic conditions and spread into a layer of even thickness. A 4.4 cm×4.4 cm piece of collagen sponge was placed on the top of the spread gel, and it was covered with another layer of cross-linked HA gel (6.8 mg/ml, 4±0.1 ml). The collagen sponge was allowed to soak in the gel for 16 hours under aseptic condition in a refrigerator. The mold containing the composite was frozen at −46° C. and then freeze-dried for 24 hours under a vacuum of less than 10 millimeters. The freeze-dried composite was compressed under aseptic conditions and cut into 3.5 cm×3.5 cm pieces. These sponges were put in sterile pouches and sealed to keep them sterile. The amount of cross-linked HA present in Sponge 2A was 2.6±0.2 mg/cm$^2$.

Example 6

Example 6 describes the preparation of Sponge 2B, an embodiment of the invention which is a composite including cross-linked HA on both sides of a porous, pliable, biocompatible, biodegradable support made of collagen from bovine tendon. The collagen, similar to that used in Example 5, was one-half the density of the normal collagen sponges sold under the name, Helistat®.

The tendon collagen matrix was cut in to 4.4 cm×4.4 cm square pieces. These pieces were heat sterilized in a vacuum oven at 140° C. for 4 hours. After cooling under aseptic conditions, cross-linked HA gel (3.8 mg/ml, 3±0.1 ml), prepared according to the procedure described in Example 1, was poured in to a 4.4 cm×4.4 cm mold under aseptic conditions and spread into a layer of even thickness. A 4.4 cm×4.4 cm piece of collagen sponge was placed on the top of it and it was covered with another layer of cross-linked HA gel (3.8 mg/ml, 4±0.1 ml). The collagen sponge was allowed to soak in the gel for 1 hour under aseptic condition in a refrigerator. The mold containing the composite was frozen at −46° C. and then freeze-dried for 24 hours under vacuum of less then 10 millimeters. The freeze-dried composite was compressed under aseptic conditions and cut into 3.5 cm×3.5 cm pieces. These sponges were put in sterile pouches and sealed to keep them sterile. The amount of cross-linked HA present in Sponge 2B was 1.42±0.05 mg/cm$^2$.

Example 7

This example describes the preparation of an embodiment of the invention, Sponge 7, a composite having HA derivative on both sides of a support made of collagen. The HA derivative has at least about 1% cross-linking, and was prepared according to the following procedure.

A solution of hyaluronic acid (M. Wt. 2.35×10$^6$ Daltons, 1922 ml, 6 mg/ml, pH 4.75, 28.76 mmoles) in saline was cross-linked using a solution of cross-linker p-phenylene-bis(ethylcarbodiimide) in acetone (1 mg/ml, 246 ml, 1.15 mmoles). The cross-linked HA was precipitated, separated from the solution and washed with ethanol. A weighed portion of the precipitate was dissolved in sterile water to form cross-linked HA gel of ~7.7 mg/ml concentration.

Non-sterile collagen sponge was cut in to square pieces of desired dimensions. Cross-linked HA gel (7.7 mg/ml, 24 ml), prepared according to the procedure described above was poured in to the lower chamber of a 12 cm×8 cm mold and spread into a layer of even thickness. A 14 cm×10 cm piece of collagen sponge was placed on the top of the spread gel and it was covered with another layer of cross-linked HA gel (7.7 mg/ml, 24 ml). The collagen sponge was allowed to soak in the gel for 1 hour under aseptic condition in a refrigerator. The mold containing the composite was frozen at −46° C. and then freeze-dried for 24 hours under vacuum of less then 10 millimeters. The freeze-dried composite was compressed and its sides were trimmed to make a sponge, 11.5 cm×7.5. This larger piece of sponge was then cut in to four 5.5 cm×3.5 cm pieces. Each piece was individually packed in a pouch made from spun-bonded olefin, sealed and sterilized by ethanol. The amount of cross-linked HA present in the composite, Sponge 7, was 4.3 mg/cm$^2$.

Example 8

This example describes the preparation of an embodiment of the invention, Sponge 8, a composite having HA derivative on both sides of a support made of collagen. The HA derivative has at least about 8% crosslinking, and was prepared according to the following procedure. A solution of hyaluronic acid (M. Wt. 0.76×10$^6$ Daltons, 404 ml, 6 mg/ml, pH 4.75, 6.0 mmoles) in saline, was cross-linked with a solution of cross-linker p-phenylene-bis(ethylcarbodiimide) in acetone (1 mg/ml, 51.7 ml, 0.24 mmoles).

The cross-linked HA was precipitated, separated from the solution, and washed with ethanol. A weighed portion of the precipitate was dissolved in sterile water to obtain cross-linked HA gel of ~7.5 mg/ml concentration.

Non-sterile collagen sponge, custom-made by Collagen Matrix Inc. (Lot #123098) was cut into square pieces. Cross-linked HA gel (7.5 mg/ml, 24 ml), was poured into the lower chamber of a 12 cm×8 cm mold and spread to form a layer of even thickness. An 11.5 cm×7.5 cm piece of collagen sponge was placed on the top of the cross-linked HA gel layer, and the sponge was covered with another layer of cross-linked HA gel (7.5 mg/ml, 24 ml). The collagen sponge was allowed to soak in the gel for 1 hour under aseptic conditions in a refrigerator. The mold containing the composite was frozen at −46° C. and then freeze-dried for 24 hours under vacuum of less then 10 millimeters. The freeze-dried composite was compressed and its sides were trimmed to make a composite sponge of 11.5×7.5 cm. This larger piece was then cut into four 5.5×3.5 cm pieces. Each piece was individually packed in a pouch made from spun-bonded olefin, sealed and sterilized by ethyl alcohol. The amount of cross-linked HA present in the composite, Sponge 8, was 4.2 mg/cm$^2$.

Example 9

The study described in this example was undertaken to evaluate the effectiveness of embodiments of the invention, versus a comparative device, as prophylaxis against adhesions in a peritoneum model involving traumatization of the caecum in rabbits. The HA derivative used in the study was prepared according to the procedure described in Example 1 of the invention.

Five groups (A through E) of twelve rabbits per group comprised this study. The animals in Group-A were treated with sponges (Sponge 1) and the density of the cross-linked HA (or chemically modified HA) in these sponges was 6.1±0.8 mg/cm$^2$. Group-B and Group-C animals were treated with Sponge 2 and Sponge 3, respectively. The density of the cross-linked HA in these composites were 4.7±0.8 mg/cm$^2$ and 1.3±0.5 mg/cm$^2$, respectively. The animals in Group-D were treated with a commercially available comparative device, Seprafilm®, and served as a positive control. (Seprafilm® is a registered trademark of Genzyme Corporation.) The animals in Group-E were untreated and served as a control.

The experimental animal was a male/female Bastard rabbit weighing between 2.5–3.5 kg and 3–4 months of age. The animals were anesthetized with 0.05 mg atropine and ether for anesthesia. Their abdomens were prepared for surgery by shearing, shaving and disinfecting the abdominal skin. The abdominal cavity was exposed by median laparotomy causing the eventration of appendix and small intestine. The visceral peritoneum adjacent to the wall defect was traumatized. The surface of the caecum was carefully rubbed with a sterile gauze compress for 15 minutes. Spotty hemorrhage occurred at the surface followed by hemorrhaging surface. Visceral peritoneum that was associated with the remaining intestinal loop was also traumatized using the same procedure for 5 minutes. A 3×3 cm piece of the peritoneum of the underlying transverse abdominal muscle was excised from the right side of the abdominal wall. A 4×4 cm piece of each test sample (Sponge 1, Sponge 2, Sponge 3, and Seprafilm®) was implanted in such a way as to overlap the defect. The implants, Sponge 2 and Sponge 3, were each fixed at the four corners with surgical sutures, made from a polyglyconate, available commercially as Maxon® USP4/0. Maxon® is a registered trademark of American Cyanamid Co. Corp. The wounds were closed, and the animals were allowed to recover.

Twenty-one days following surgery, all animals in each group were sacrificed and their abdomens examined for the presence of adhesions in the window of the abdominal wall. The tenacity of adhesion was determined with a tensiometer by measuring the force required to separate the adhered tissues. The adhesion was measured as the ratio of the size of the window in the abdominal wall and the area of adhesion.

The incidence of adhesion formation and tenacity of each adhesion was determined and compared between the treated and untreated (control) animals. The validity of a test article being able to prevent the development of an adhesion was determined by statistical analysis of the reduction of incidence rate and tenacity of adhesion between the treated and untreated animals.

As shown in Table 1, the sponge used in Group-A (Sponge 1) and the composites used in Group-B and Group-C (Sponge 2 and Sponge 3) were all effective as anti-adhesion compositions. Sponge-1 and Sponge-2 materials out-performed the Seprafilm® positive control. In the case of Sponge-3, performance was somewhat inferior to Seprafilm®
and this is likely due to the lower concentration of cross-linked HA used in this material.

experiment served as a positive control and control, respectively.

The animals used in this study and the study protocol were the same as described above in Example 9.

A 3.5×3.5 cm piece of the test sample (Sponge 2A, Sponge 2B) was implanted in each of the test animals and fixed at the four corners with surgical sutures. The wounds were closed and animals were allowed to recover.

Twenty-one days following surgery, all animals in each group were sacrificed and their abdomens examined for the

TABLE 1

Example 9, Testing in Animal Model

| Group | Name of the Device | Description of the Device | Density of Mod. HA (mg/cm$^2$) | Number of Rabbits | Number of Animals with Adhesion | % Tenacity |
|---|---|---|---|---|---|---|
| A | Sponge 1 | Sponge (Mod. HA only) | 6.1 ± 0.8 | 11 | 2/12 (16.6%) | 11.25 ± 11.8 |
| B | Sponge 2 | Composite (Gelatin, HA deriv., both sides) | 4.7 ± 0.8 | 11 | 2/12 (16.6%) | 15.70 ± 11.03 |
| C | Sponge 3 | Composite (Gelatin, HA deriv., both sides) | 1.3 ± 0.5 | 9 | 7/9 (77.7%) | 12.30 ± 5.71 |
| D | Comparison | Seprafilm® | | 11 | 6/11 (54.5%) | 8.0 ± 2.95 |
| E | Control | Control | | 11 | 11/11 (100%) | 26.36 ± 11.93 |

Example 10

The study described in this example was undertaken to evaluate the effectiveness of the composites of cross-linked HA and collagen (Sponge 2A and 2B) as prophylaxis against adhesions in a peritoneum model involving traumatization of the caecum in rabbits.

Two groups (A and B) of twelve rabbits per group comprised this study. The animals in Group-A were treated with Sponge 2A and the density of the cross-linked HA in these composites was 2.6±0.2 mg/cm$^2$. Animals in Group-B were treated with Sponge 2B and the density of the cross-linked HA in the composites used was 1.4±0.05 mg/cm$^2$. The animals of Group-D and Group-E of the previous experiment served as a positive control and control, respectively.

presence of adhesions in the window of the abdominal wall, the tenacity of adhesion determined by measuring the force of removal with a tensiometer, and the ratio of the size of the window in the abdominal wall and the area of adhesion measured.

The validity of a test article being able to prevent the development of an adhesion was determined by statistical analysis of the reduction of incidence rate and tenacity of adhesion between the treated and untreated animals.

As shown in Table 2, the composites used in Group-A (Sponge-2A) and Group-B (Sponge-2B) were effective as anti-adhesion compositions. In each case, the sponge materials (2A and 2B) out-performed the Seprafilm® positive control.

TABLE 2

Example 10, Testing in Animal Model, Collagen Support

| Group | Name of the Device | Description of the Device | Density of Mod. HA (mg/cm$^2$) | No. of Rabbits | Number of Animals with Adhesion | % Tenacity |
|---|---|---|---|---|---|---|
| A | Sponge 2A | Collagen Support, HA | 2.6 ± 0.2 | 12 | 4/12 (33.3%) | 1.6 ± 0.4 |
| B | Sponge 2B | Collagen Support, HA | 1.4 ± 0.05 | 12 | 5/12 (41.6%) | 1.9 ± 0.53 |
| D | Comparison | Seprafilm® | | 11 | 6/11 (54.5%) | 8.0 ± 2.95 |
| E | Control | Control | | 11 | 11/11 (100%) | 26.36 ± 11.93 |

Example 11

The study described in this example was undertaken to evaluate the effectiveness of two composites of this invention in prevention of pericardial adhesion in a rabbit model.

Animals: 50 New Zealand White rabbits (*Oryctolagus cuniculus*), weighing 2.8 to 3.3 kg. The study was performed in accordance with the NIH guidelines as described in the Guide for the Care and Use of Laboratory Animals, National Academy Press, 1996.

Study Design
The following treatment groups were used:

A. Control         D. Gel, HA derivative only
B. Sponge 8        E. Comparative Seprafilm® II (Genzyme Corp.)
C. Sponge 7

The study investigated vectorial information about effective size and variance.

Surgical Procedure

The rabbit pericardial adhesion model was conducted essentially as described by Wiseman et al. (J. Surg. Res. Vol. 53, pp. 362–8 (1992)) with minor modifications. Briefly, after anesthesia was induced by intramuscular injection of a mixture of ketamine 50 mg and xylazine 10 mg/ml, 1 mL/Kg, the thorax was entered via a median sternotomy and a median pericardotomy performed. A standard abrasion was made on the anterior (ventral) surface using dry two-ply gauze. On completion of abrasion and attainment of hemostasis the surgeon was made aware of the random assignment. Sponges 8 and 7 and Separafilm® II were each cut in an elliptical shape to cover the anterior cardiac surface in Groups B, C, and E animals, respectively. In Group D animals, a gel including HA derivative only, 2.5 ml, was applied via syringe and gently spread over the anterior cardiac surface. Controls consisted of animals undergoing sham surgery, receiving no material.

Between 28 and 30 days post surgery animals were euthanatized by intravenous injection of 120 mg/mL/kg of sodium pentobarbital and the heart and anterior thoracic wall dissected en bloc. The extent, tenacity and density of adhesions were noted on the posterior side of the heart, the lateral borders and the anterior surface of the heart.

The primary efficacy parameter evaluated for each animal was the percentage length of adhesion involvement of the "central strip." The "central strip" is a 1 cm strip of anterior (ventral) ventricle epicardium extending from the apex of the heart caudally to the atrioventricular junction. This is the area most likely to form adhesions in a consistent manner.

Secondary parameters evaluated included the tenacity and density of adhesions, as well as, epicardial visibility. The percent length involvement of the lateral epicardium and the posterior (dorsal) epicardium were noted. These parameters were scored on a scale of 0 (no adhesions/completely visible) to 3 (severe adhesions/completely obliterated).

Tenacity of Adhesions (Secondary Parameter)

Assessments of adhesion tenacity were made at each location, i.e.,

0=no adhesions
1=filmy adhesions easily separable by blunt dissection
2=more cohesive adhesions separable by aggressive blunt or mild sharp dissection
3=strongly cohesive adhesions that require aggressive sharp dissection.

Density of Adhesions (Secondary Parameter)

0=no adhesions
1=sparse distribution of adhesions, many gaps observed between individual bands
2=adhesions occurring in clumps, some free areas noted within overall involved area
3=adhesions completely covering the involved area.

Evaluations were made by the same observer blinded as to the group assignment of the particular animal. For each treatment group and location the mean length of adhesions (±SEM) was calculated and compared to controls. As the term is used herein, "SEM" refers to the mean standard deviation for each group, and is obtained by dividing the average deviation for each sample by the square root of the number of samples. The average % extent for the left and right anterior surface was taken for each animal and used to calculate the mean lateral adhesion extent for the group. Tenacity, density and visibility scores along the central strip were compared against controls using the $x^2$ test.

Photographs were taken of the surgical procedure and during the dissection of representative specimens. Representative specimens were placed into neutral buffered formalin for histology. At least one specimen per group was taken without dissection of the lateral or anterior surfaces of the epicardium. The results of Example 11 are summarized in Table 3 below, and in the FIGURE.

TABLE 3

Results of Example 11

Effect of Cross-linked Hyaluronan Formulations on Pericardial Adhesion Formation vs. Comparative and Control in the Rabbit Model

| Group | No. of animals | Central Strip %[1] | T[2] | D[3] | Visibility[4] | Lateral[5] |
|---|---|---|---|---|---|---|
| A: Control | 11 | Mean 80.45 | 2.5 | 2.8 | 1.7 | 54.3 |
|  |  | SEM 8.5 | 0.2 | 0.2 | 0.2 | 9.6 |
| B: Sponge 8 | 6 | Mean 53.3 | 1.5 | 1.83 | 1.8 | 40 |
|  |  | SEM 8.4 | 0.2 | 0.2 | 0.4 | 5.9 |
| C: Sponge 7 | 11 | Mean 53.6 | 1.2 | 2.0 | 1.3 | 40.2 |
|  |  | SEM 9.05 | 0.1 | 0.2 | 0.3 | 7.2 |
| D: Gel, HA derivative only | 10 | Mean 34.6† | 1.4 | 1.8 | 1.3 | 18.6 |
|  |  | SEM 8.24 | 0.2 | 0.2 | 0.4 | 8.5 |
| E: Comparative (Seprafilm® II) | 11 | Mean 50.5‡ | 1.6 | 2.1 | 1.5 | 33.9 |
|  |  | SEM 6.76 | 0.1 | 0.2 | 0.2 | 8.4 |

[1] % of Central Strip with adhesions
[2] Mean tenacity of adhesions along central strip
[3] Mean density of adhesions along central strip
[4] Mean visibility: ability to visualize epicardial vessels (0–3 scale)
[5] Average % length involved with adhesions for left and right anterior epicardial surfaces
† $p < 0.01$ Dunnett's t test vs. control
‡ $p < 0.05$ Dunnett's t test vs. control Reduction in the extent, tenacity and density of adhesions were noted with all test materials, the greatest reductions being observed with the cross-linked derivative gel only. The average percentage area of adhesion for the gel only was 35%, as compared to 80% for the untreated control. All of the test materials were easy to handle and apply and no adverse effects attributable to the use of the materials were noted.

While this invention has been particularly shown and described with references to preferred embodiments thereof, those skilled in the art will recognize or be able to ascertain using no more than routine experimentation, many equivalents to embodiments of the invention described specifically herein. Such equivalents are intended to be encompassed in the scope of the following claims.

What is claimed is:

1. A composite for reducing post-operative adhesion of tissues, comprising:
   a) a biocompatible, biodegradable support; and
   b) a hyaluronic acid derivative at the support, said hyaluronic acid derivative comprising an N-acylurea that results from reaction of hyaluronic acid with a multifunctional carbodiimide.

2. The composite of claim 1, wherein the hyaluronic acid derivative is water insoluble.

3. The composite of claim 1, wherein the multifunctional carbodiimide employed to form the N-acylurea is a biscarbodiimide.

4. The composite of claim 3, wherein the biscarbodiimide has the structure:

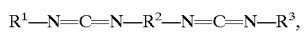

where $R^1$, $R^2$ and $R^3$ are each independently selected from the group consisting of hydrocarbyl, substituted-hydrocarbyl, alkoxy, aryloxy, and alkaryloxy groups.

5. The composite of claim 4, wherein the biscarbodiimide is p-phenylene-bis(ethyl carbodiimide).

6. The composite of claim 4, wherein the biscarbodiimide is selected from the group consisting of:
   1,6-hexamethylene bis(ethylcarbodiimide);
   1,8-octamethylene bis(ethylcarbodiimide);
   1,10 decamethylene bis(ethylcarbodiimide);
   1,12 dodecamethylene bis(ethylcarbodiimide);
   PEG-bis(propyl(ethylcarbodiimide));
   2,2'-dithioethyl bis(ethylcarbodiimde);
   1,1'-dithio-p-phenylene bis(ethylcarbodiimide); and
   1,1'-dithio-m-phenylene bis(ethylcarbodiimide).

7. The composite of claim 3, wherein the hyaluronic acid derivative is at least about 1% cross-linked.

8. The composite of claim 7, wherein the cross-linked hyaluronic acid derivative is in the form of a sponge.

9. The composite of claim 7, wherein the cross-linked hyaluronic acid derivative is in the form of a film.

10. The composite of claim 7, wherein the cross-linked hyaluronic acid derivative is in the form of a gel.

11. The composite of claim 7, wherein the support is porous, and a portion of the cross-linked hyaluronic acid derivative covers a surface of the support, and another portion of the cross-linked hyaluronic acid derivative is within pores of the support.

12. The composite of claim 11, wherein the cross-linked hyaluronic acid has a first biodegradation rate and the support has a second biodegradation rate, wherein said first biodegradation rate is faster than said second biodegradation rate at room temperature, and wherein, upon biodegradation and removal of at least a portion of the cross-linked hyaluronic acid covering the surface of the support, at least a portion of the cross-linked hyaluronic acid remains in the pores of the support when the composite is in use in vivo.

13. The composite of claim 1, wherein at least 2% of carboxyl functionalities of the hyaluronic acid have been derivatized.

14. The composite of claim 13, wherein at least 25% of the derivatized functionalities are O-acylisoureas or N-acylureas.

15. The composite of claim 1, wherein the support is selected from the group consisting of cross-linked alginates, gelatin, collagen, cross-linked collagen, collagen derivatives, cross-linked hyaluronic acid, chitosan, chitosan derivatives, cellulose and derivatives thereof, dextran derivatives, polyanionic polysaccharides and derivatives thereof, polylactic acid (PLA), polyglycolic acid (PGA), a copolymer of a polylactic acid and a polyglycolic acid (PLGA), lactides, glycolides, polyoxanones, polyoxalates, copolymer of poly(bis(p-carboxyphenoxy)propane) anhydride (PCPP) and sebacic acid, poly(1-glutamic acid), poly(d-glutamic acid), polyacrylic acid, poly(d1-glutamic acid), poly(1-aspartic acid), poly(d-aspartic acid), poly(d1-aspartic acid), polyethylene glycol, copolymers of polyamino acids with polyethylene glycol, polypeptides, polycaprolactone, poly(alkylene succinates), poly(hydroxy butyrate) (PHB), poly(butylene diglycolate), nylon-2/nylon-6-copolyamides, polydihydropyrans, polyphosphazenes, poly(ortho ester), poly(cyano acrylates), polyvinylpyrrolidone, and polyvinylalcohol.

16. The composite of claim 15, wherein the support is a polypeptide selected from the group consisting of polycasein, keratin, myosin, and fibrin.

17. The composite of claim 1, wherein the hyaluronic acid derivative comprises a first layer, and the biocompatible, biodegradable support comprises a second layer having at least one surface in contact with said first layer.

18. The composite of claim 1, wherein the support has at least two distinct sides and the hyaluronic acid derivative is located on at least one of the two sides.

19. The composite of claim 1, wherein the support is a matrix.

20. The composite of claim 19, wherein the matrix is porous.

21. The composite of claim 20, wherein the matrix is a sponge.

22. The composite of claim 1, wherein the support is a film.

23. The composite of claim 1, wherein the support is a composite of particles.

24. The composite of claim 23, wherein the particles are beads.

25. The composite of claim 24, wherein the beads are porous and are bound together by a bioabsorbable material.

26. The composite of claim 1, further including a pharmaceutically-active molecule.

27. The composite of claim 26, wherein the pharmaceutically-active molecule is selected from the group consisting of growth factors, enzymes, therapeutic drugs, biopolymers, and biologically compatible synthetic polymers.

28. The composite of claim 1, further including a material that enhances adherence of the composite to tissue.

29. The composite of claim 28, wherein the material that enhances adherence to tissue is a polymer containing the peptide sequence, arginine (R), glycine (G), and aspartic acid (D).

30. The composite of claim 28, wherein the material that enhances adherence of the composite to tissue is a polymer selected from the group consisting of fibrin, collagen, cross-linked collagen, and collagen derivatives.

31. A composite for reducing post-operative adhesion of tissues, comprising:
   a) a biocompatible, biodegradable support; and
   b) a hyaluronic acid derivative at the support, said hyaluronic acid derivative comprising an N-acylurea that results from reaction of hyaluronic acid with a multifunctional carbodiimide wherein at least 25% of derivatized functionalities of the hyaluronic acid derivative are O-acylisoureas or N-acylureas.

32. The composite of claim 31, wherein the hyaluronic acid derivative has been cross-linked by the multifunctional carbodiimide.

33. The composite of claim 32, wherein the carbodiimide is a biscarbodiimide.

34. A drug delivery vehicle, comprising:
   a) a biocompatible, biodegradable support;
   b) a hyaluronic acid derivative component at the biocompatible, biodegradable support, said hyaluronic acid derivative component comprising an N-acylurea that is formed by reaction of hyaluronic acid with a multifunctional carbodiimide; and
   c) a pharmaceutically active molecule at the hyaluronic acid derivative component.

35. The drug delivery vehicle of claim 34, wherein the hyaluronic acid derivative component is cross-linked with a multifunctional carbodiimide.

36. The drug delivery vehicle of claim 34, wherein the multifunctional carbodiimide is a biscarbodiimide.

37. The drug delivery vehicle of claim 34, wherein at least one side arm of the N-acylurea is bonded to the pharmaceutically-active molecule.

38. The drug delivery vehicle of claim 34, wherein the pharmaceutically-active molecule is selected from the group consisting of growth factors, enzymes, therapeutic drugs, biopolymers, and biologically compatible synthetic polymers.

39. A composite for reducing post-operative adhesion of tissues, comprising:
   a) a biocompatible, biodegradable support; and
   b) a hyaluronic acid derivative at the support, said hyaluronic acid derivative comprising an N-acylurea that results from reaction of hyaluronic acid with a mixture of a multifunctional carbodiimide and a monocarbodiimide.

40. The composite of claim 39, wherein said monocarbodiimide is of the formula:

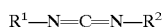

in which $R^1$ and $R^2$ are each independently selected from the group consisting of hydrocarbyl, substituted-hydrocarbyl, alkoxy, aryloxy, alkylaryloxy.

41. The composite of claim 39, wherein said monocarbodiimide is selected from the group consisting of:
   1-ethyl-3-(3-dimethylaminopropyl)-carbodiimide hydrochloride (EDC);
   1-cyclohexyl-3-(2-morpholinoethyl)carbodiimide metho-p-toluenesulfonate (CMC);
   1-(3-(dimethylamino)propyl)-3-ethylcarbodiimide methiodide (EAC);
   1,3-dicyclohexylcarbodiimide (DCC); and
   1-benzyl-3-(3-dimethylaminopropyl) carbodiimide hydrochloride (BDC).

42. The composite of claim 39, wherein the multifunctional carbodiimide is a biscarbodiimide.

43. The composite of claim 39, wherein the multifunctional carbodiimide is a biscarbodiimide having the structure:

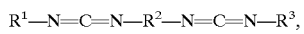

where $R^1$, $R^2$ and $R^3$ are each independently selected from the group consisting of hydrocarbyl, substituted-hydrocarbyl, alkoxy, aryloxy, and alkaryloxy groups.

44. The composite of claim 43, wherein the biscarbodiimide is p-phenylene-bis(ethyl carbodiimide).

45. The composite of claim 43, wherein the biscarbodiimide is selected from the group consisting of:
   1,6-hexamethylene bis(ethylcarbodiimide);
   1,8-octamethylene bis(ethylcarbodiimide);
   1,10 decamethylene bis(ethylcarbodiimide);
   1,12 dodecamethylene bis(ethylcarbodiimide);
   PEG-bis(propyl(ethylcarbodiimide));
   2,2'-dithioethyl bis(ethylcarbodiimde);
   1,1'-dithio-p-phenylene bis(ethylcarbodiimide); and
   1,1'-dithio-m-phenylene bis(ethylcarbodiimide).

46. The composite of claim 39, further including a pharmaceutically active molecule at the hyaluronic acid derivative component.

47. The composite of claim 46, wherein at least one side arm of the N-acylurea is bonded to the pharmaceutically-active molecule.

48. The composite of claim 46, wherein the pharmaceutically-active molecule is selected from the group consisting of growth factors, enzymes, therapeutic drugs, biopolymers, and biologically compatible synthetic polymers.

49. A method of forming a composite for reducing post-operative adhesion of tissues, comprising the step of applying a hyaluronic acid derivative to a biocompatible, biodegradable support, said hyaluronic acid derivative comprising an N-acylurea that results from reaction of hyaluronic acid with a multifunctional carbodiimide.

50. The method of claim 49, wherein the hyaluronic acid derivative formed is water insoluble.

51. The method of claim 49, wherein the multifunctional carbodiimide is a biscarbodiimide.

52. The method of claim 51, wherein the biscarbodiimide has the structure:

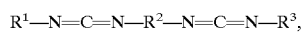

where $R^1$, $R^2$ and $R^3$ are each independently selected from the group consisting of hydrocarbyl, substituted hydrocarbyl, alkoxy, aryloxy, and alkaryloxy groups.

53. The method of claim 52, wherein the cross-linked hyaluronic acid derivative is cross-linked with p-phenylene-bis(ethylcarbodiimide).

54. The method of claim 52, wherein the cross-linked hyaluronic acid derivative is cross-linked with a biscarbodiimide selected from the group consisting of:
   1,6-hexamethylene bis(ethylcarbodiimide);
   1,8-octamethylene bis(ethylcarbodiimide);
   1,10 decamethylene bis(ethylcarbodiimide);
   1,12 dodecamethylene bis(ethylcarbodiimide);
   PEG-bis(propyl(ethylcarbodiimide));
   2,2'-dithioethyl bis(ethylcarbodiimde);
   1,1'-dithio-p-phenylene bis(ethylcarbodiimide); and
   1,1'-dithio-m-phenylene bis(ethylcarbodiimide).

55. The method of claim 51, wherein the hyaluronic acid derivative is at least about 1% cross-linked.

56. The method of claim 49, wherein the support is selected from the group consisting of cross-linked alginates, gelatin, collagen, cross-linked collagen, collagen derivatives, cross-linked hyaluronic acid, chitosan, chitosan derivatives, such as, methylpyrrolidone-chitosan, cellulose and derivatives thereof, dextran derivatives, polyanionic polysaccharides and derivatives thereof, polylactic acid (PLA), polyglycolic acid (PGA), a copolymer of a polylactic acid and a polyglycolic acid (PLGA), lactides, glycolides, polyoxanones, polyoxalates, copolymer of poly(bis(p-carboxyphenoxy)propane)anhydride (PCPP) and sebacic acid, poly(1-glutamic acid), poly(d-glutamic acid), polyacrylic acid, poly(dl-glutamic acid), poly(l-aspartic acid), poly(d-aspartic acid), poly(dl-aspartic acid), polyethylene glycol, copolymers of polyamino acids with polyethylene glycol, polypeptides, polycaprolactone, poly(alkylene succinates), poly(hydroxy butyrate) (PHB), poly(butylene diglycolate), nylon-2/nylon-6-copolyamides, polydihydropyrans, polyphosphazenes, poly(ortho ester), poly(cyano acrylates), polyvinylpyrrolidone, and polyvinylalcohol.

57. The method of claim 49, wherein the support is a sponge.

58. The method of claim 49, wherein the support is a film.

59. The method of claim 49, wherein the hyaluronic acid derivative is applied to the support by spreading the hyaluronic acid derivative on at least one surface of the support to form a composite.

60. The method of claim 49, wherein the hyaluronic acid derivative is applied to the support by spraying the hyaluronic acid derivative on at least one surface of the support to form a composite.

61. The method of claim 49, wherein the hyaluronic acid derivative is applied to the support by dipping at least one surface of the support in the hyaluronic acid derivative to form a composite.

62. The method of claim 49, wherein the support includes porous beads.

63. The method of claim 62, wherein the hyaluronic acid derivative is applied to the beads by soaking the beads in the hyaluronic acid derivative, allowing the hyaluronic acid derivative to be absorbed and adsorbed by the pores of the beads, and drying the beads.

64. The method of claim 63, further including the step of compressing the beads to form a sheet.

65. The method of claim 63, comprising the further steps of suspending the dried beads in a solution of a solvent and a second biopolymer; pouring the suspension into a mold; and evaporating the solvent.

66. The method of claim 65, wherein the second biopolymer is a polylactic—polyglycolic acid—copolymer (PLGA).

67. The method of claim 49, wherein the hyaluronic acid derivative is applied to the support by a method that includes the step of molding a water insoluble gel of hyaluronic acid derivative at the support.

68. The method of claim 67, further including a step wherein a material that enhances adherence of the composite to tissue is molded at the support.

69. The method of claim 68, wherein the material that enhances adherence to tissue is a polymer containing the peptide sequence, arginine (R), glycine (G), and aspartic acid (D).

70. The method of claim 49, further including the step of at least partially drying the hyaluronic acid derivative on the biocompatible, biodegradable support.

71. A method for reducing post-operative adhesion of tissues, comprising the step of introducing to the tissues at a surgical site a composite that includes a biocompatible, biodegradable support, and a derivatized hyaluronic acid component at the support, said derivatized hyaluronic acid component having been formed by reaction of hyaluronic acid with a multifunctional carbodiimide.

72. The method of claim 71, wherein the carbodiimide is a biscarbodiimide, and the modified hyaluronic acid has been cross-linked by the biscarbodiimide.

73. The method of claim 71, wherein the composite further includes a pharmaceutically-active molecule.

74. A method for delivering a pharmaceutically-active molecule, comprising delivering to a surgical site a composite that includes a biocompatible, biodegradable support, a hyaluronic acid derivative, said hyaluronic acid derivative comprising an N-acylurea that results from reaction of hyaluronic acid with a multifunctional carbodiimide and a pharmaceutically-active molecule.

75. The method of claim 74, wherein the multifunctional carbodiimide is a biscarbodiimide.

76. The method of claim 74, wherein at least one side-arm of the N-acylurea is bonded to the pharmaceutically-active molecule.

77. A method of preparing a drug delivery vehicle, comprising the step of applying a hyaluronic acid derivative component to a biocompatible, biodegradable support, said hyaluronic acid derivative component comprising an N-acylurea that results from reaction of hyaluronic acid with a multifunctional carbodiimide, and a pharmaceutically-active molecule.

78. The method of claim 77, wherein the hyaluronic acid derivative component is cross-linked with the multifunctional carbodiimide.

79. The method of claim 78, wherein the multifunctional carbodiimide is a biscarbodiimide.

80. The method of claim 77, wherein at least one side arm of the N-acylurea is bonded to the pharmaceutically-active molecule.

81. The method of claim 77, wherein the pharmaceutically-active molecule is selected from the group consisting of growth factors, enzymes, therapeutic drugs, biopolymers, and biologically compatible synthetic polymers.

82. The method of claim 77, further including the step of at least partially drying the hyaluronic acid derivative component on the biocompatible, biodegradable support.

83. A method of forming a composite for reducing post-operative adhesion of tissues, comprising the step of applying a hyaluronic acid derivative component to a biocompatible, biodegradable support, said hyaluronic acid derivative component comprising an N-acylurea that results from reaction of hyaluronic acid with a multifunctional carbodiimide and a monocarbodiimide.

84. The method of claim 83, wherein said monocarbodiimide is of the formula:

$$R^1-N=C=N-R^2$$

in which $R^1$ and $R^2$ are each independently selected from the group consisting of hydrocarbyl, substituted-hydrocarbyl, alkoxy, aryloxy, alkylaryloxy.

85. The method of claim 84, wherein said monocarbodiimide is selected from the group consisting of:
  1-ethyl-3-(3-dimethylaminopropyl)-carbodiimide hydrochloride (EDC);
  1-cyclohexyl-3-(2-morpholinoethyl)carbodiimide metho-p-toluenesulfonate (CMC);
  1-(3-(dimethylamino)propyl)-3-ethylcarbodiimide methiodide (EAC);
  1,3-dicyclohexylcarbodiimide (DCC); and
  1-benzyl-3-(3-dimethylaminopropyl)carbodiimide hydrochloride (BDC).

86. The method of claim 83, wherein the multifunctional carbodiimide is a biscarbodiimide.

87. The method of claim 86, wherein the biscarbodiimide has the structure:

$$R^1-N=C=N-R^2-N=C=N-R^3,$$

where $R^1$, $R^2$ and $R^3$ are each independently selected from the group consisting of hydrocarbyl, substituted-hydrocarbyl, alkoxy, aryloxy, and alkaryloxy groups.

88. The method of claim 87, wherein the biscarbodiimide is p-phenylene-bis(ethyl carbodiimide).

89. The method of claim 87, wherein the biscarbodiimide is selected from the group consisting of:
  1,6-hexamethylene bis(ethylcarbodiimide);
  1,8-octamethylene bis(ethylcarbodiimide);
  1,10 decamethylene bis(ethylcarbodiimide);
  1,12 dodecamethylene bis(ethylcarbodiimide);
  PEG-bis(propyl(ethylcarbodiimide));
  2,2'-dithioethyl bis(ethylcarbodiimde);
  1,1'-dithio-p-phenylene bis(ethylcarbodiimide); and
  1,1'-dithio-m-phenylene bis(ethylcarbodiimide).

* * * * *